US009833463B2

(12) United States Patent
Omwancha et al.

(10) Patent No.: US 9,833,463 B2
(45) Date of Patent: Dec. 5, 2017

(54) SITAGLIPTIN TANNATE COMPLEX

(71) Applicants: MERCK SHARP & DOHME CORP., Rahway, NJ (US); Wycliffe Omwancha, Kenilworth, NJ (US); Rubi Burlage, Kenilworth, NJ (US)

(72) Inventors: Wycliffe Omwancha, East Brunswick, NJ (US); Rubi Burlage, Florham Park, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/302,211

(22) PCT Filed: Apr. 13, 2015

(86) PCT No.: PCT/US2015/025504
§ 371 (c)(1),
(2) Date: Oct. 6, 2016

(87) PCT Pub. No.: WO2015/160678
PCT Pub. Date: Oct. 22, 2015

(65) Prior Publication Data
US 2017/0042922 A1 Feb. 16, 2017

Related U.S. Application Data

(60) Provisional application No. 61/980,641, filed on Apr. 17, 2014.

(51) Int. Cl.
A01N 43/04 (2006.01)
A61K 31/70 (2006.01)
A61K 31/7032 (2006.01)
A61K 31/4985 (2006.01)
C07D 487/04 (2006.01)
A61K 45/06 (2006.01)
A61K 31/235 (2006.01)
A61K 9/00 (2006.01)
A61K 31/496 (2006.01)

(52) U.S. Cl.
CPC ........ A61K 31/7032 (2013.01); A61K 9/0053 (2013.01); A61K 31/235 (2013.01); A61K 31/496 (2013.01); A61K 31/4985 (2013.01); A61K 45/06 (2013.01); C07D 487/04 (2013.01)

(58) Field of Classification Search
None
See application file for complete search history.

(56) References Cited

U.S. PATENT DOCUMENTS

| 5,663,415 A | 9/1997 | Chopdekar et al. |
| 6,670,370 B1 | 12/2003 | Chopdekar et al. |
| 6,699,871 B2 | 3/2004 | Edmondson et al. |
| 6,881,741 B2 | 4/2005 | Chan Chun Kong et al. |
| 6,939,856 B2 | 9/2005 | Redkar et al. |
| 7,326,708 B2 | 2/2008 | Cypes et al. |
| 7,547,806 B2 | 6/2009 | Frenkel et al. |
| 2003/0083354 A1 | 5/2003 | Keil et al. |
| 2005/0202050 A1 | 9/2005 | Kiel et al. |
| 2013/0177604 A1 | 7/2013 | Baron et al. |

FOREIGN PATENT DOCUMENTS

| WO | WO2003004498 A1 | 1/2003 |
| WO | WO2005003135 A1 | 1/2005 |
| WO | WO2005020920 A2 | 3/2005 |
| WO | WO2005030127 A2 | 4/2005 |
| WO | WO2005072530 A1 | 8/2005 |
| WO | WO2006033848 A1 | 3/2006 |
| WO | WO2007035198 A2 | 3/2007 |
| WO | WO2010092090 A2 | 8/2010 |

OTHER PUBLICATIONS

Ogawa et al. Tohoku J. Exp. Med. (2011), vol. 223, pp. 133-135.*
Augustyns, K., Dipeptidyl peptidase IV inhibitors as new therapeutic agents for the treatment of Type 2 diabetes, Expert Opin.Ther. Patents, 2003, p. 499-510, vol. 13, No. 4.
Deacon, Carolyn, F., Dipeptidyl peptidase IV inhibition as an approach to the treatment and prevention of type 2 diabetes: a historical perspective, Biochemical and Biophysical Research Communications, 2002, p. 1-4, vol. 294.
Drucker, Daniel, J., Therapeutic potential of dipeptidyl peptidase IV inhibitors for the treatment of type 2 diabetes, Expert Opin. Investig. Drugs, 2003, p. 87-100, vol. 12, No. 1.
Vummaneni, V. et al, Taste Masking Technologies: An Overview and Recent Updates, International Journal of Research in Pharmaceutical and Biomedical Sciences, 2012, p. 510-524, vol. 3, No. 2.

* cited by examiner

Primary Examiner — Patrick T Lewis
(74) Attorney, Agent, or Firm — Baerbel R. Brown; Catherine D. Fitch

(57) ABSTRACT

The present invention provides for a sitagliptin tannate complex or a pharmaceutical compositions or a pharmaceutically acceptable intermediates comprising said complex. This invention also relates to a processes to prepare the sitagliptin tannate complex as well as to methods of using the sitagliptin tannate complex to treat diabetes, obesity and high blood pressure.

15 Claims, 3 Drawing Sheets

SITAGLIPTIN TANNATE COMPLEX

CROSS-REFERENCE TO RELATED APPLICATIONS

This application is a U.S. National Phase application under 35 U.S.C. §371 of PCT Application No. PCT/US2015/025504, filed on Apr. 13, 2015, which claims priority from and the benefit of U.S. Provisional Application No. 61/980,641, filed Apr. 17, 2014.

FIELD OF THE INVENTION

The present application relates to a complex of sitagliptin (4-oxo-4-[3-(trifluoromethyl)-5,6-dihydro[1,2,4] triazolo[4,3-a] pyrazin-7(8H)-yl]-1-(2,4,5-trifluorophenyl)butan-2-amine) and tannic acid ("sitagliptin tannate complex"), which is a potent inhibitor of dipeptidyl peptidase-IV ("DPP-IV"). This novel tannate complex is useful for the treatment, control or prevention of diseases and conditions for which an inhibitor of DPP-IV is indicated. This invention further relates to an oral dosage form comprising an effective amount of the sitagliptin tannate complex, a pharmaceutical intermediate comprising an effective amount of the sitagliptin tannate complex, methods of treating, controlling or preventing a disease or condition for which a DPP-IV inhibitor is indicated by administering an effective amount of the sitagliptin tannate complex to a patient in need thereof, and a process to prepare the sitagliptin tannate complex.

BACKGROUND OF THE INVENTION

Inhibition of DPP-IV, an enzyme that inactivates both glucose-dependent insulinotropic peptide (GIP) and glucagon-like peptide 1 (GLP-1), represents a novel approach to the treatment and prevention of type 2 diabetes, also known as non-insulin dependent diabetes mellitus (NIDDM). The therapeutic potential of DPP-IV inhibitors for the treatment of type 2 diabetes has been reviewed: C. F. Deacon and J. J. Holst, "Dipeptidyl peptidase IV inhibition as an approach to the treatment and prevention of type 2 diabetes: a historical perspective," *Biochem. Biophys. Res. Commun.*, 294: 1-4 (2000); K. Augustyns, et al., "Dipeptidyl peptidase IV inhibitors as new therapeutic agents for the treatment of type 2 diabetes," *Expert. Opin. Ther. Patents*, 13: 499-510 (2003); and D. J. Drucker, "Therapeutic potential of dipeptidyl peptidase IV inhibitors for the treatment of Type 2 diabetes," *Expert Opin. Investig. Drugs*, 12: 87-100 (2003).

WO2003/004498, assigned to Merck Sharp & Dohme Corp., describes a class of beta-amino tetrahydrotriazolo[4,3-a]pyrazines, which are potent inhibitors of DPP-IV, and therefore are useful for the treatment of type 2 diabetes. Specifically disclosed in WO 03/004498 is 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. While pharmaceutically acceptable salts of this compound are generically encompassed within the scope of WO 03/004498, there is no specific disclosure the sitagliptin tannate complex.

WO2005/003135, also to Merck Sharp & Dohme Corp., discloses the dihydrogenphosphate salt of sitagliptin. The publication indicates that the dihydrogenphosphonate salt is a potent inhibitor of DPP-IV and, therefore, is useful for the treatment and prevention of non-insulin dependent diabetes mellitus, also referred to as type 2 diabetes, obesity and high blood pressure. WO2005/003135 also describes a crystalline monohydrate of the dihydrogenphosphate salt as well as a process for its preparation, pharmaceutical compositions containing this novel salt form, and methods of use for the treatment of type 2 diabetes, obesity, and high blood pressure. WO2005/003135 does not describe a sitagliptin tannate complex. WO2005/072530, WO2006/033848, and WO2007/035198, all to Merck Sharp & Dohme Corp., describe salts of sitagliptin.

Tannic acid, also known as tannin, gallotannin, glycerite or gallotannin, is a yellowish to light brown amorphous powder having the approximate composition of $C_{76}H_{52}O_{46}$ and a molecular weight of about 1701 grams/mol. Although tannic acid is typically produced from Turkish or Chinese nutgall, it can be derived from the bark and fruit of many plants. Tannic acid is very soluble in water, glycerin or alcohol. Tannic acid may be obtained either by extraction from natural products or through synthetic chemical synthesis.

Tannate complexes comprising pharmaceutically active compounds are known in the art. See, e.g., U.S. Pat. No. 5,663,415; U.S. Pat. No. 6,881,741 B2; U.S. Pat. No. 6,939,856 B2; U.S. Pat. No. 6,670,370 B1; and U.S. Pat. No. 7,547,806 B2. Tannate salts have been found to have better organoleptic properties, such as taste, in comparison to other salts or free base forms. See, e.g., US 2005/0202050 A1 or US 2003/0083354 A1. Additionally, Vummaneni et al. (*International Journal of Research in Pharmaceutical and Biomedical Sciences* 3(2), 510-524 (2012)) report that tannic acid acts as a taste masker for chloroquine phosphate. Moreover, as tannate salts are relatively large molecules, they afford absorption of the pharmaceutically active compound over a prolonged period of time and hence can be used in sustained release preparations. See, e.g., U.S. Pat. No. 7,547,806 B2; US 2005/0202050 A1 or US 2003/0083354 A1.

Sitagliptin as a monohydrate phosphate salt is the active ingredient in JANUVIA® and one of the active agents in JANUMET® AND JANUMET XR®, all marketed by Merck Sharp & Dohme Corp., a subsidiary of Merck & Co., Inc., to improve glycemic control in adults with type 2 diabetes mellitus. An unintended effect of sitagliptin monohydrate phosphate is that it has an intense, lingering bitter taste. In order to overcome this bitter taste, drug products containing sitagliptin monohydrate phosphate are formulated as a film-coated tablet. Marketing sitagliptin monohydrate phosphate as a film-coated tablet is not always ideal as an estimated 20% of the patients taking JANUMET® experience a difficulty in swallowing the tablet.

Hence, there is a need to develop alternative intra-oral dosage forms with a pleasant taste for patient populations (e.g., the elderly or children) who cannot swallow the large tablets. Moreover, any of these alternative intra-oral dosage forms must be relatively easy to manufacture to make the product cost effective. This and other objectives will become evident from the following description.

SUMMARY OF THE INVENTION

In its many embodiments, the present invention is directed to a tannate complex of sitagliptin, to an oral dosage form comprising an effective amount of the sitagliptin tannate complex, a pharmaceutical intermediate comprising an effective amount of the sitagliptin tannate complex, and to methods of treating, controlling, or preventing a disease or condition for which a DPP-IV inhibitor is indicated by administering an effective amount of the sitagliptin tannate complex to a patient in need thereof. This invention further relates to processes to prepare the sitagliptin tannate complex.

Applicants discovered that the sitagliptin tannate complex possesses a release property or profile in which the sitagliptin tannate complex exhibits a negligible release rate at neutral pH, such as that found in the mouth, and immediate release in acidic pH, such as that found in the stomach. This release property allows one to formulate sitagliptin in oral dosage form that is easier to swallow and does not need a film layer, e.g., a dosage form such as a chewable tablet, soft chew, medicated gum or disintegrating table, because the sitagliptin tannate complex has a neutral taste in the mouth. Moreover, oral dosage forms that have a neutral taste would be expected to improve patient compliance in taking the medicine.

Further, this release property is unexpected in view of what the prior art generally teaches about tannate complexes. The prior art discloses that tannate complexes impart extended release properties to a pharmaceutical formulation comprising an active pharmaceutical ingredient (API) (see, e.g., U.S. Pat. No. 6,670,370 and U.S. Pat. No. 6,939,856). Exhibiting extended release properties implies that the API in an extended release pharmaceutical formulation is stable (i.e., exhibits negligible dissociation) in acidic pH, such as that found in the stomach, and dissociates in a predefined manner over time in neutral pH, such as that found in the intestine. However, in the release property of the inventive sitagliptin tannate complex, unexpectedly the opposite occurs in that the immediate release occurs at acidic pH.

DETAILED DESCRIPTION OF THE INVENTION

Figure 1:
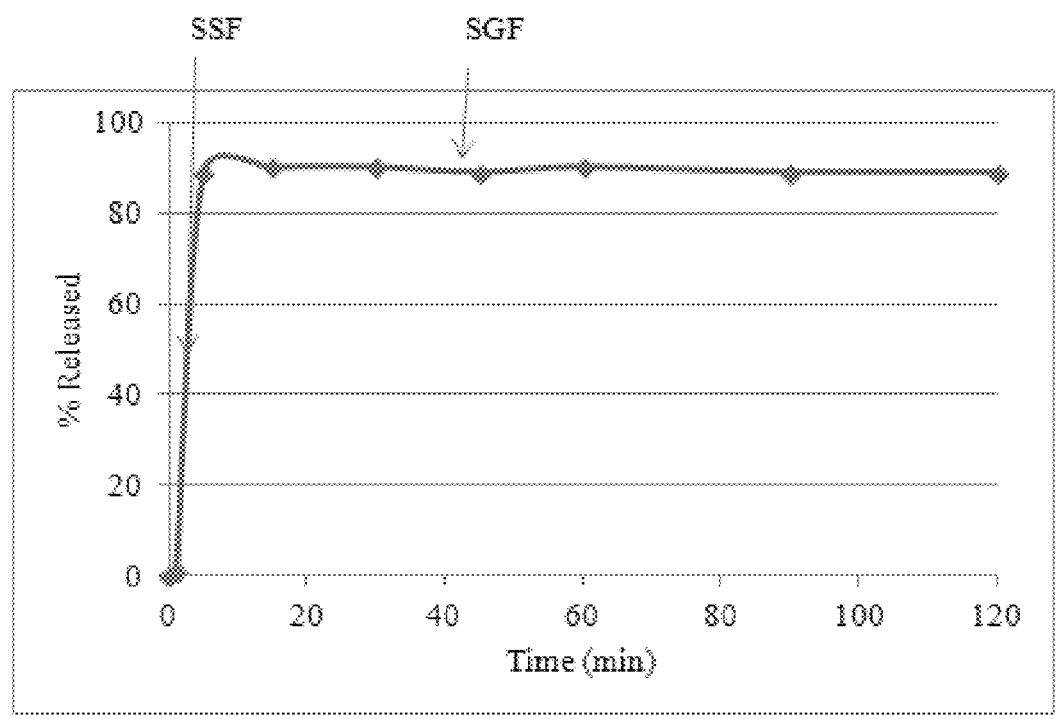
FIG. 1 is graph depicting the two-stage dissolution profile for the sitagliptin tannate complex of Example 1. The graph plots the percentage (%) of sitagliptin released from the sitagliptin tannate complex versus time.

In an embodiment, this invention provides for a sitagliptin tannate complex.

Another embodiment of the present invention is a sitagliptin tannate complex wherein the sitagliptin content is between about 25% and about 75% by weight or between about 29% and 33% by weight.

Another embodiment of the present invention is a sitagliptin tannate complex wherein the ratio of sitagliptin to tannic acid is about 3:1 to about 1:4 by weight; for example about 1:2 by weight.

Another embodiment of the present invention is a pharmaceutical composition comprising a therapeutically effective amount of the sitagliptin tannate complex according to claim 1 and an inert carrier.

Another embodiment of the present invention is a pharmaceutical composition comprising a therapeutically effective amount of the sitagliptin tannate complex according to claim 1, a therapeutically effective amount of at least one additional pharmaceutically active ingredient (e.g., a biguanide such as metformin or a pharmaceutically acceptable salt thereof) and an inert carrier.

Another embodiment of the present invention is a pharmaceutical intermediate, which comprises a pharmaceutically effective amount of a sitagliptin tannate complex, a pharmaceutically acceptable polymer (e.g., polyethylene glycol (PEG), such as PEG 3350, PEG 6000 or PEG 8000), and optionally, one or more pharmaceutically acceptable polyols (e.g., mannitol or maltitol), high intensity sweeteners (e.g., sucralose) or flavorants (e.g., mint, cherry or banana flavor).

Another embodiment of the present invention is an oral dosage form (e.g. a tablet, capsule, pellet or powder), which comprises the pharmaceutical intermediate comprising a therapeutically effective amount of a sitagliptin tannate complex.

Another embodiment of the present invention is an oral dosage form, which comprises the pharmaceutical intermediate comprising a therapeutically effective amount of a sitagliptin tannate complex and the oral dosage form is in the form of a soft chew, medicated gum, chewable tablet, disintegrating tablet, syrup, sachet, oral film, gel or lyosphere.

Another embodiment of the present invention is an oral dosage form (e.g., a soft chew, medicated gum, oral film, disintegrating tablet or syrup), which comprises the pharmaceutical intermediate comprising a therapeutically effective amount of a sitagliptin tannate complex, wherein the sitagliptin has negligible release in the mouth and immediate release in the stomach.

Another embodiment of the present invention is a method for treating, controlling or preventing of one or more diseases for which an inhibitor of DPP-IV is indicated comprising the administration a therapeutically effective amount of the sitagliptin tannate complex to a patient in need thereof.

Another embodiment of the present invention is a method for treating, controlling or preventing type 2 diabetes, obesity and high blood pressure comprising the administration of a therapeutically effective amount of the sitagliptin tannate complex to a patient in need thereof.

Another embodiment of the present invention is the use of a sitagliptin tannate complex for the manufacture of a medicament for the treatment and/or prevention of one or more diseases for which an inhibitor of DPP-IV is indicated.

As used throughout the specification, the following terms, unless otherwise indicated, shall be understood to have the following meanings:

"Patient" includes both human and other animals.

"Mammal" includes humans and other mammalian animals.

The term "therapeutically effective amount" is intended to mean that amount of a pharmaceutically active ingredient that will elicit the biological or medical response of a tissue or a system, animal or human, that is being sought by a researcher, veterinarian, medical doctor or other clinician (e.g., inhibiting DPP-IV). A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" are used herein to refer to administering a compound before the onset of clinical symptoms.

The term "immediate release" means that at least 85% of the drug is released from the dosage form within 120 minutes or less when tested in a USP type 2 apparatus in a fasted state simulated intestinal fluid (FaSSIF) at a pH of 6.5 at room temperature (approximately 25° C.), which can be made using SIF™ powder (from biorelevant.com Ltd) as follows:

Step 1. Preparation of the FaSSIF buffer (5 L)
1.1 To prepare 5 L, dissolve the following in approximately 4.9 L of purified water:
2.10 g NaOH (pellets), 19.77 g sodium hydrogen phosphate monohydrate (or alternatively, 17.19 g sodium dihydrogen phosphate anhydrous), and 30.93 g NaCl.
1.2 Adjust the pH of the buffer to exactly 6.5, using either 1N NaOH or 1N HCL, and make up to volume.

Step 2. Preparation of FaSSIF using SIF™ powder (1 L);
2.1 In a 1 L volumetric flask, dissolve 2.24 g of SIF™ powder (stored at 5° C. and equilibrated at room temperature prior to use) in approximately 500 ml of the FaSSiF phosphate buffer.
2.2 Stir until the SIF™ powder has dispersed. When a clear solution is obtained, make up to volume (1 L) with the FaSSIF phosphate buffer.

The term "negligible release" means that the amount of sitagliptin dissociated from the sitagliptin tannate complex is not sufficient for the sitagliptin tannate complex to lose its tastemasking activity in a subject; e.g., up to 10% of the sitagliptin is dissociated from the sitagliptin tannate complex, up to 5% of the sitagliptin is dissociated from the sitagliptin tannate complex, or up to 3% of the sitagliptin is dissociated from the sitagliptin tannate complex.

The term "pharmaceutical composition" is intended to encompass both bulk compositions and individual dosage units comprised of more than one (e.g., two) pharmaceutically active agents such as, for example, the sitagliptin tannate complex and an additional active ingredient. Examples of other pharmaceutically active ingredients that may be administered in combination with the sitagliptin tannate complex of the present invention, and either administered separately or in the same pharmaceutical composition, include, but are not limited to:

(a) other DPP-IV inhibitors;
(b) insulin sensitizers including (i) PPARγ agonists such as the glitazones (e.g. troglitazone, pioglitazone, englitazone, MCC-555, rosiglitazone, and the like) and other PPAR ligands, including PPAR α/γ dual agonists, such as KRP-297, and PPARα agonists such as fenofibric acid derivatives (gemfibrozil, clofibrate, fenofibrate and bezafibrate), (ii) biguanides such as metformin HCl and phenformin, and (iii) protein tyrosine phosphatase-1B (PTP-1B) inhibitors;
(c) insulin or insulin mimetics;
(d) sulfonylureas and other insulin secretagogues such as tolbutamide and glipizide, meglitinide, and related materials;
(e) α-glucosidase inhibitors (such as acarbose);
(f) glucagon receptor antagonists such as those disclosed in WO 98/04528, WO 99/01423, WO 00/39088, and WO 00/69810;
(g) GLP-1, GLP-1 mimetics, and GLP-1 receptor agonists such as those disclosed in WO00/42026 and WO00/59887;
(h) GIP and GIP mimetics such as those disclosed in WO00/58360, and GIP receptor agonists;
(i) PACAP, PACAP mimetics, and PACAP receptor 3 agonists such as those disclosed in WO 01/23420;
(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPAR γ agonists such as fenofibric acid derivatives (gemfibrozil, clofibrate, fenofibrate and bezafibrate), (v) PPAR α/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;
(k) PPAR δ agonists, such as those disclosed in WO97/28149;
(l) anti-obesity compounds such as fenfluramine, dexfenfluramine, phentermine, sibutramine, orlistat, neuropeptide Y5 inhibitors, and $\beta_3$ adrenergic receptor agonists;
(m) an ileal bile acid transporter inhibitor; and
(n) agents intended for use in inflammatory conditions such as aspirin, non-steroidal anti-inflammatory drugs, glucocorticoids, azulfidine, and cyclo-oxygenase 2 selective inhibitors.

The above combinations include combinations of the sitagliptin tannate complex of the present invention not only with one other pharmaceutically active ingredient, but also with two or more different pharmaceutically active ingredients. Non-limiting examples include combinations of the sitagliptin tannate complex with two or more pharmaceutically active ingredients selected from biguanides, sulfonylureas, HMG-CoA reductase inhibitors, PPAR agonists, PTP-1B inhibitors, other DPP-IV inhibitors, and anti-obesity compounds.

The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of oral dosage forms containing 0.01, 0.05, 0.1, 0.5, 1.0, 2.5, 5.0, 10.0, 15.0, 25.0, 50.0, 100, 200, and 500 milligrams of sitagliptin for the symptomatic adjustment of the dosage to the patient to be treated. A medicament typically contains from about 0.01 mg to about 500 mg of sitagliptin, preferably, from about 1 mg to about 200 mg of active ingredient.

In the method of the present invention the sitagliptin tannate complex can form the active pharmaceutical ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the active pharmaceutical ingredient can be combined with any oral, non-toxic, pharmaceutically acceptable inert carrier such as ethanol, glycerol, water and the like. Moreover, when desired or necessary, additional pharmaceutically acceptable adjuvants may be added. Additional pharmaceutical adjuvants include binders, lubricants, sweeteners, flavoring agents, disintegrating agents and coloring agents, which are known in the art (see, e.g., Remington's Pharmaceutical Sciences (1995). Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

General Method for Preparing a Sitagliptin Tannate Complex

The sitagliptin tannate complex of the present invention can be made by the following process:

(1) Combine a solution of a salt for free base form of sitagliptin in a pharmaceutically acceptable solvent (e.g., methanol or ethanol) with a dispersion of tannic acid in a pharmaceutically acceptable solvent (e.g., methanol or ethanol), while stirring, to form a first mixture;

(2) Remove most of the liquid from the first mixture by, for example, evaporation, decantation or vacuum drying;

(3) Wash the residue obtained in step (2) with a polar pharmaceutically acceptable liquid (e.g., water);

(4) Remove all the liquid from the washed residue obtained in step (3) by, for example, evaporation, decantation or vacuum drying;

(5) Dry the residue obtained in step (4), for example, in a vacuum oven (e.g. at 50° C.) for about 3 to 10 hours, to provide the sitagliptin tannate complex;

(6) Pulverize the sitagliptin tannate complex (e.g., via milling) into a free-flowing powder.

EXAMPLES

Sitgliptin Tannate Complexes

Example 1

The active solution of sitagliptin was prepared by dissolving 0.5 g of sitagliptin freebase in 20 ml of methanol. 1 g of tannic acid was dissolved in the same amount of methanol to form tannic acid dispersion. The sitagliptin solution was then added slowly to tannic acid dispersion while stirring. The mixture was allowed to stir until all the solvent evaporated under ambient conditions in a fume hood. The solid material formed was pulverized into powder. 100 ml of water was added to the powder and the mixture stirred for 30 minutes, before centrifuging at 15K rpm to remove the liquid. The washed sitagliptin tannate complex was then dried in a constant temperature oven at 50° C.

Example 2

A solution of 1.5 g sitagliptin freebase and a dispersion of 3 g tannic acid were prepared separately in 20 ml of ethanol. Small portions of sitagliptin solution were added to tannic acid dispersion while stirring. After all the sitagliptin solution was added, the mixture was allowed to stir under ambient conditions in a fume hood until all the solvent evaporated. The solid material was further dried in a vacuum oven at 50° C. for about 3 hours. It was then pulverized into a powder.

Two Stage Dissolution Profile

The dissolution profile of the sitagliptin tannate complexes of Example 1 and 2 using simulated saliva fluid (SSF) and simulated gastric fluid (SGF) by using the following two stage dissolution protocol:

Stage 1: A sample of sitagliptin tannate complex of Example 1 or 2 was placed in 10 mL of SSF, which was prepared by dissolving 8.0 g of NaCl, 0.19 g of potassium phosphate monobasic, and 2.38 g of sodium phosphate dibasic in 1 L of water, and adjusting to pH 6.8 with phosphoric acid, heated to 37° C., for 1 minute and an aliquot was removed.

Stage 2: The remaining solution transferred to 500 mL of SGF, which was prepared by dissolving 2.0 g of NaCl in 1 L of water, and adding 1.4 mL of concentrated hydrochloric acid. The SGF was stirred at 37° C. with apparatus 2 (paddles), and aliquots were collected at 6 time-points.

The aliquots were then analyzed by HPLC to determine the amount of free sitagliptin.

Figure 2:
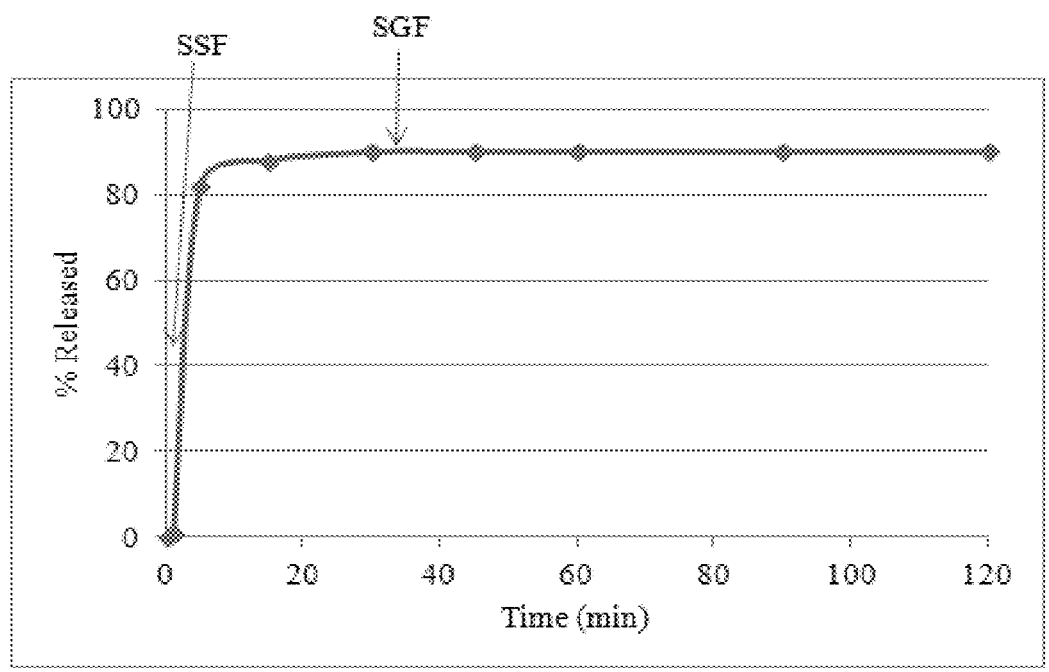
FIG. 2 is a graph depicting the two-stage dissolution profile for the sitagliptin tannate complex of Example 2. The graph plots the percentage (%) of sitagliptin released from the sitagliptin tannate complex versus time.
Figure 3:
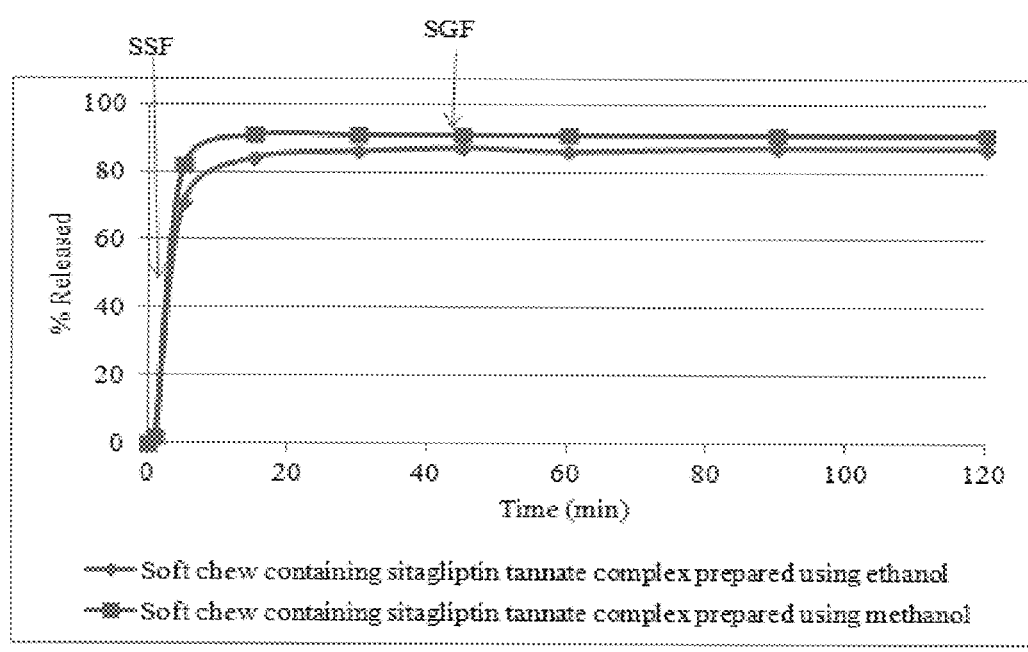
FIG. 3 is a graph depicting the two-stage dissolution profile for a soft-chew formulation comprising the sitagliptin tannate complex of Example 3. The graph plots the percentage (%) of sitagliptin released from the sitagliptin tannate complex in the soft-chew formulation versus time.

FIG. 1 depicts the dissolution profile of Example 1 and FIG. 2 depicts the dissolution profile of Example 2. Both profiles indicate that very little to no sitagliptin was released in SSF. This indicates that the sitagliptin-tannic acid complex is not soluble or almost not soluble at neutral pH and, hence, a subject would not be expected to taste the unpleasant flavor of sitagliptin. However, in both profiles, the sitagliptin is rapidly released from the complex at the low pH of SGF and, therefore, would be expected to be available for absorption by the subject.

Formulation Example

Soft Chew

The sitagliptin tannate complexes obtained in Examples 1 and 2 were formulated as a soft chew by incorporating the sitagliptin tannate complex of the following composition:

| PART | Ingredient | % w/w |
|------|-----------|-------|
| A | glycerin USP | 5.0 |
| A | MAGNASWEET ® 100 (ammonium glycyrrhizate) | 0.1 |
| A | sucralose | 0.5 |
| C | sitagloptin tannate complex of Example 1 or Example 2 | 10.0 |
| A | LYCASIN ® 85/55 (maltitol syrup) | 25.0 |
| B | partially hydrogentated palm kernel oil (Paramount C) | 12.0 |
| B | PEG 8000 | 3.0 |
| B | glycerol monostearate | 0.5 |
| C | MALTRIN ® M040 (maltodextrin) | 18.4 |
| C | Starch1500 ® | 25.0 |
| D | peppermint | 0.5 |

The soft chew formulation was prepared as follows:
(1) The ingredients of part A were mixed until uniform;
(2) The ingredients of part B were mixed;
(3) The ingredients of part C were mixed in a turbular mixer for about 10 minutes;
(4) The mixed ingredients from step (2) were melted and added to the mixed ingredients of step (1) and mixed well;

(5) The mixed ingredients from step (3) were added to the mixed ingredient from step (4) and mixed until uniform;

(6) Peppermint was added to the mixture obtained in step (5) and mixed well to obtain a dough-like mixture;

(7) The dough-like mixture was placed into a soft-chew mold and allowed to congeal and form the soft-chew units containing the sitagliptin tannate complex of Example 1 or Example 2.

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. All patents, patent applications and publications cited herein are incorporated by reference in their entirety.

What is claimed is:

1. Sitagliptin tannate complex.

2. The sitagliptin tannate complex according to claim 1, wherein the sitagliptin content is between about 25% and about 75% by weight.

3. The sitagliptin tannate complex according to claim 2, wherein the sitagliptin content is between about 29 and about 33% by weight.

4. The sitagliptin tannate complex according to claim 1, wherein the ratio of sitagliptin to tannic acid is about 3:1 to about 1:4 by weight.

5. The sitagliptin tannate complex according to claim 4, wherein the ratio is about 2:1 by weight.

6. A pharmaceutical composition comprising a therapeutically effective amount of the sitagliptin tannate complex according to claim 1 and an inert carrier.

7. The pharmaceutical composition according to claim 6 that further comprises a therapeutically effective amount of an additional pharmaceutically active ingredient.

8. A pharmaceutical intermediate which comprises a therapeutically effective amount of a sitagliptin tannate complex according to claim 1, a pharmaceutically acceptable polymer, and, optionally, one or more polyols, high intensity sweeteners, flavorants.

9. An oral dosage form which comprises the pharmaceutical intermediate according to claim 8.

10. The oral dosage form according to claim 9, which is in the form of a tablet, capsule, pellet or powder.

11. The oral dosage form according to claim 9, which is in the form of a soft chew, medicated gum, chewable tablet, disintegrating tablet, syrup, sachet, oral film, gel or lyosphere.

12. The oral dosage form according to claim 9, which has negligible release in the mouth and immediate release in the stomach.

13. The oral dosage form according to claim 12, which is a soft chew, medicated gum, oral film, disintegrating tablet or syrup.

14. A method for treating, controlling, or preventing of one or more diseases for which an inhibitor of DPP-IV is indicated, comprising the administration a therapeutically effective amount of the sitagliptin tannate complex according to claim 1 to a patient in need thereof.

15. The method according to claim 14, wherein the disease is type 2 diabetes, obesity or high blood pressure.

* * * * *